United States Patent [19]
Hayes

[11] 3,939,102
[45] *Feb. 17, 1976

[54] HYDROCARBON ISOMERIZATION CATALYST AND PROCESS

[75] Inventor: John C. Hayes, Palatine, Ill.

[73] Assignee: Universal Oil Products Company, Des Plaines, Ill.

[ * ] Notice: The portion of the term of this patent subsequent to Oct. 1, 1991, has been disclaimed.

[22] Filed: Mar. 29, 1974

[21] Appl. No.: 456,705

Related U.S. Application Data

[63] Continuation-in-part of Ser. No. 365,782, May 31, 1973, Pat. No. 3,839,193, which is a continuation-in-part of Ser. No. 27,457, April 10, 1970, abandoned.

[52] U.S. Cl. ............... 252/439; 252/441; 252/442; 260/668 A; 260/683.2; 260/683.68
[51] Int. Cl.² . B01J 27/04; B01J 27/08; B01J 27/10
[58] Field of Search ................... 252/441, 439, 442

[56] References Cited
UNITED STATES PATENTS

| | | | |
|---|---|---|---|
| 2,848,377 | 8/1958 | Webb | 252/441 X |
| 3,507,781 | 4/1970 | Spurlock et al. | 252/442 X |
| 3,632,525 | 1/1972 | Rausch | 252/439 X |
| 3,654,184 | 4/1972 | McCallister et al. | 252/442 |
| 3,839,193 | 10/1974 | Hayes | 252/441 X |

Primary Examiner—Patrick P. Garvin
Attorney, Agent, or Firm—James R. Hoatson, Jr.; Thomas K. McBride; Wiliam H. Page, II

[57] ABSTRACT

A hydrocarbon isomerization catalyst composition, comprising a combination of catalytically effective amounts of a platinum or palladium component, an iridium component, a germanium component, a halogen component and a Friedel-Crafts metal halide component combined with a refractory inorganic oxide is disclosed. A specific example of the disclosed catalytic composition is a combination of catalytically effective amounts of a platinum component, an iridium component, a germanium component, a chloride component and an aluminum chloride component with an alumina carrier material, effective in isomerizing a pentane-hexane hydrocarbon fraction or in isomerizing non-equilibrium mixtures of alkylaromatic hydrocarbons such as xylenes.

9 Claims, No Drawings

HYDROCARBON ISOMERIZATION CATALYST AND PROCESS

CROSS-REFERENCES TO RELATED APPLICATIONS

This application is a continuation-in-part of my copending application Ser. No. 365,782 filed May 31, 1973, now U.S. Pat. No. 3,839,193, Oct. 1, 1974 which copending application is a continuation-in-part of my copending application Ser. No. 27,457, filed Apr. 10, 1970, now abandoned the teachings of both of which copending applications are specifically incorporated herein by reference.

BACKGROUND OF THE INVENTION

This invention relates to a catalyst for isomerizing isomerizable hydrocarbons including isomerizable parraffins, cycloparafins, olefins and alkylaromatics. This invention further relates to a process for isomerizing isomerizable hydrocarbons with a catalytic composite comprising a combination of platinum or palladium component, an iridium component, a germanium component, a halogen component and a Fridel-Crafts metal halide with a refractory inorganic oxide. The present invention utilizes a dual-function catalytic composite having both a hydrogenation-dehydrogenation function and a cracking function which affords substantial improvements in hydrocarbon isomerization processes that have traditionally used dual-function catalysts.

Processes for the isomerization of hydrocarbons have acquired significant importance within the petrochemical and petroleum refining industry. The demand for para-xylene has created a demand for processes to isomerize other xylene isomers and ethylbenzene to produce para-xylene. The demand for certain branched chain paraffins, such as isobutane or isopentane, as intermediates in producing high octane motor fuel alkylate, can be met by isomerizing the corresponding normal paraffins. It is desired that the alkylate be highly branched to provide a high octane rating. This can be accomplished by alkylating an isoparaffin with $C_4$-$C_7$ internal olefins which, in turn, can be produced by isomerization of corresponding linear alpha-olefins.

Catalytic composites exhibiting a dual hydrogenation-dehydrogenation and cracking function are widely used in the petroleum and petrochemical industry to isomerize hydrocarbons. Such catalysts generally have a heavy metal component, e.g., metals or metallic compounds of Group V through VIII of the Periodic Table, to inpart a hydrogenation-dehydrogenation function, with an acid-acting inorganic oxide to import a cracking function. In catalysis of isomerization reactions, it is important that the catalytic composite not only catalyze the specific desired isomerization reaction by having its dual hyrogenation-dehydrogenation function correctly balanced against its cracking function, but also that the catalyst perform its desired functions well over prolonged periods of time.

The performance of a given catalyst in a hydrocarbon isomerization process is typically measured by the activity, selectivity, and stability of the catalyst. Activity refers to the ability of a catalyst to isomerize the hydrocarbon reactants into the corresponding isomers at a specified set of reaction conditions; selectivity refers to the percent of reactants isomerized to form the desired isomerized product and/or products; stability refers to the rate of change of the selectivity and activity of the catalyst.

The principal cause is instability (i.e., loss of selectivity and activity in an originally selective, active catalyst) is the formation of coke on the catalytic surface of the catalyst during the reaction. This coke is characterizable as a high molecular weight, hydrogen-deficient, carbonaceous material, typically having an atomic carbon to hydrogen ratio of about 1 or more. Thus, a problem in the hydrocarbon isomerization art is the development of more active and selective composites not sensitive to the carbonaceous materials and/or having the ability to suppress the rate of the formation of these carbonaceous materials on the catalyst. A primary aim of the art is to develop a hydrocarbon isomerization process utilizing a dual-function catalyst having superior activity, selectivity and stability. In particular, it is desired to provide a process wherein hyrocarbons are isomerized without excessive cracking or other decomposition reactions which lower the overall yield of the process and make it more difficult to operate.

SUMMARY OF THE INVENTION

It is an object of this invention to provide a catalyst composition suitable for use in a process for isomerizing isomerizable hydrocarbons. It is another object of this invention to provide an isomerization process using a particular isomerization catalyst effective in isomerizing isomerizable hydrocarbons without introducing undesired decomposition and/or cracking reactions. It is a further object of this invention to provide a process for isomerizing isomerizable hydrocarbons utilizing a dual-function catalyst having superior activity, selectivity and stability.

An isomerization process has now been developed utilizing a dual-function catalyst which possesses improved activity, selectivity and stability. Moreover, in the particular case of a $C_8$ alkylaromatic isomerization process, the present catalyst allows essentially equilibrium conversions of the $C_8$ alkylaromatics with essentially stoichiometric selectivity without evidencing excessive production of hydrogenated or cracked products. Further, this activity and selectivity is readily maintainable at its originally high levels, evidencing a very stable catalytic alkylaromatic isomerization process.

In a broad embodiment, this invention relates to a catalytic composite comprising a refractory inorganic oxide having combined therewith, on a Friedel-Crafts metal halide-free basis, about 0.01 to about 2 weight percent platinum or palladium, about 0.01 to about 2 weight percent iridium, about 0.01 to about 5 weight percent germanium, and about 0.1 to about 3.5 weight percent halogen, calculated on an elemental basis, and about 1.0 to about 100 weight percent Friedel-Crafts metal halide, wherein the platinum or palladium, iridium and germanium are uniformly dispersed throughout the refractory inorganic oxide, wherein substantially all of the platinum or palladium and iridium are present in the corresponding metallic states and wherein substantially all of the germanium is present in an oxidation state above that of the elemental metal.

In another broad embodiment, this invention relates to a process for isomerizing an isomerizable hydrocarbon which comprises contacting said hydrocarbon at isomerization conditions with a catalytic composite comprising a combination of a platinum or palladium component, as iridium component, a germanium component, a halogen component and a Friedel-Crafts metal halide component with a refractory inorganic oxide carrier material.

In a more limited embodiment, this invention relates to a catalyst composition which comprises a combination of a platinum component, an iridium component, a germanium component, a chlorine component and an aluminum chloride component with an alumina carrier material.

In another more limited embodiment, this invention relates to an isomerization process utilizing a catalytic composite comprising a combination of a platinum or palladium component, an iridium component, a germanium component, a chlorine component and an aluminum chloride component with an alumina carrier material, the components preferably being present in the composite in amounts sufficient to result in the final composite containing, on an elemental, Friedel-Crafts metal halide-free basis, about 0.01 to about 2.0 weight percent platinum or palladium metal, and about 0.01 to about 2 weight percent iridium metal, and about 0.01 to about 5 weight percent germanium and about 3.5 weight percent chlorine, wherein the platinum or palladium, germanium and iridium are uniformly dispersed throughout the porous carrier material, wherein substantially all of the platinum or palladium and iridium are present in the corresponding elemental metallic state, wherein substantially all of the germanium is present in an oxidation state above that of the elemental metal.

In a more specific embodiment, this invention relates to the isomerization of either a saturated or olefinic isomerizable hydrocarbon by contacting the hydrocarbon with the catalytic composite of the present invention at isomerization conditions which include a temperature of about 0° to about 425°C., a pressure of about atmospheric to about 100 atmospheres and a liquid hourly space velocity of about 0.1 to about 10. In another limited embodiment this process related to the isomerization of an isomerizable alkylaromatic hydrocarbon by contacting the alkylaromatic with the catalytic composite of the present invention at isomerization conditions which include a temperature of about 0° to about 600°C., a pressure of about atmospheric to about 100 atmospheres, a liquid hourly space velocity of about 0.1 to about 20.0 hr.$^{-1}$ and a hydrogen to hydrocarbon mole ratio of about 1:1 to about 20:1.

Other objects and embodiments referring to alternative isomerizable hydrocarbons and to alternative catalytic compositions will be found in the following further detailed description of this invention.

DESCRIPTION OF PREFERRED EMBODIMENTS

The catalyst of this invention is useful in the isomerization of isomerizable saturated hydrocarbons including acyclic paraffins and cyclic naphthenes and is particularly suitable for the isomerization of straight chain or mildly branched chain paraffins containing 4 or more carbon atoms per molecule such as normal butane, normal pentane, normal hexane, normal heptane, normal octane, etc., and mixtures thereof. Cycloparaffins applicable are those containing at least 5 carbon atoms in the ring such as alkylcyclopentanes and cyclohexanes, including methylcyclopentane, dimethylcyclopentane, cyclohexane, methylcyclohexane, dimethylcyclohexane, etc. The catalyst of this invention is also useful for conversion of mixtures of paraffins and/or naphthenes such as those derived by selective fractionation and distillation of straight-run natural gasolines and naphthas. Such mixtures of paraffins and/or naphthenes include the so-called pentane fractions, hexane fractions, and mixtures thereof. It is not intended, however, to limit this invention to these enumerated saturated hydrocarbons and it is contemplated that straight or branched chain saturated hydrocarbons containing up to about 20 carbon atoms per molecule may be isomerized using the catalyst of the present invention with $C_4$–$C_9$ hydrocarbons being particularly preferred.

The olefins which may be isomerized using the present catalyst are generally mixtures of olefinic hydrocarbons of approximately the same molecular weight, including the 1-isomer, 2-isomer and other position isomers, capable of undergoing isomerization to olefins in which the double bond occupies a different position in the hydrocarbon chain. The catalyst of this invention can be used to provide an olefinic feedstock for motor fuel alkylation purposes containing an optimum amount of the more centrally located double bond isomers, by converting the 1-isomer, or other near-terminal-position isomer into olefins wherein the double bond is made centrally located in the carbon atoms chain. The catalyst of this invention is useful for isomerizing such isomerizable olefinic hydrocarbons as 1-butene or 3-methyl-1-butene, which are converted into 2-butene and 2-methyl-2-butene, respectively. This invention can be utilized to shift the double bond of an olefinic hydrocarbon such as 1-pentene, 1-hexene, 2-hexene or 4-methyl-1-pentene to a more centrally located position so that 2-pentene, 2-hexene, 3-hexene or 4-methyl-2pentene, respectively, can be obtained. It is not intended to limit this invention to the enumerated olefinic hydrocarbons. It is contemplated that shifting the double bond to a different position may be effective in straight or branched chain olefinic hydrocarbons containing up to about 20 carbon atoms per molecule. This invention also applies to the hydroisomerization of olefins wherein olefins are converted to branched-chain paraffins and/or branched olefins.

The catalyst of this invention is also useful for the isomerization of isomerizable alkylaromatic hydrocarbons, e.g., ortho-xylene, meta-xylene, para-xylene, ethylbenzene, the ethyltoluenes, the trimethylbenzenes, the diethylbenzenes, the triethylbenzenes, normal propylbenzene, isopropylbenzene, etc., and mixtures thereof. Preferred isomerizable alkylaromatic hydrocarbons are the alkylbenzene hydrocarbons, particularly the $C_8$ alkylbenzenes, and non-equilibrium mixtures of various $C_8$ aromatic isomers. Higher molecular weight alkylaromatic hydrocarbons such as the alkylnaphthalenes, the alkylanthracenes, the alkylphenanthrenes, etc., are also suitable.

The isomerizable hydrocarbons may be utilized as found in selective fractions from various naturally-occurring petroleum streams, e.g., as individual components or as certain boiling range fractions obtained by the selective fractionation and distillation of catalytically cracked gas oil. This invention may be utilized for complete conversion of isomerizable hydrocarbons when they are present in minor quantities in various fluid or gaseous streams. The isomerizable hydrocarbons to be converted using the catalyst of this invention need not be concentrated. For example, isomerizable hydrocarbons appear in minor quantities in various refinery offstreams, usually diluted with gases such as hydrogen, nitrogen, methane, ethane, propane, etc. These offstreams, containing minor quantities of isomerizable hydrocarbons, are obtained from various refinery installations including thermal cracking units, catalytic cracking units, thermal reforming units, coking units, polymerization units, dehydrogenation units, etc., and have in the past been burned as fuel, since an economical process for the utilization of the hydrocarbon content has not been available. This is particularly true of refinery fluid streams which contain minor quantities of isomerizable hydrocarbons. This invention allows the isomerization of aromatic streams such as reformate to produce xylenes, particularly paraxylene, thus upgrading the reformate from its gasoline value to a high petrochemical value.

As hereinbefore indicated, the catalyst of the present invention comprises a refractory inorganic oxide carrier material or support having combined therewith catalytically effective amounts of a platinum or palladium component, an iridium component, a germanium component, and a Friedel-Crafts metal halide component and a halogen component.

Considering first the porous carrier material utilized in the present invention, it is preferred that the material be a porous, adsorptive, high-surface area support having a surface area of about 25 to about 500 m$^2$/g. The porous carrier material should be relatively refractory to the conditions utilized in the present process, and it is intended to include within the scope of useable supports materials which have traditionally been utilized in dual-function hydrocarbon conversion catalysts such as: silica or silica gel, silicon carbide, clays, and silicates including those synthetically prepared and naturally-occurring, which may or may not be acid treated, for example, attapulgus clay, china clay, diatomaceous earth, fuller's earth, kaoline, kieselguhr, etc.; ceramics, porcelain, crushed firebrick, bauxite; refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; crystalline zeolitic aluminosilicates such as naturally-occurring or synthetically-prepared mordentie and/or faujasite, either in the hydrogen form or in a form which has been treated with mulit-valent cations; spinels such as Mg Al$_2$O$_4$, Fe Al$_2$O$_4$, RnAl$_2$O$_4$, MnAl$_2$O$_4$, CaAl$_2$O$_4$ and other like compounds having the formula MoAl$_2$O$_3$ wherein M is a metal having a valence of 2; and, combinations of elements from one or more of these groups. The preferred porous carrier materials for use in the catalyst employed in the present process are refractory inorganic oxides containing chemically combined hydroxyl groups such as those contained in silica and any of the other aforementioned refractory inorganic oxides including the various crystalline aluminosilicates and clays, with best results obtained with an alumina carrier material. Suitable alumina materials are the crystalline aluminas known as the gamma-, eta-. and theta-alumina, with gamma- or eta-alumina giving best results. In addition, in some embodiments the alumina carrier material may contain minor proportions of other well known refractory inorganic oxides such as silica, zirconia, magnesia, etc.; however, the preferred support is substantially pure gamma-, or eta-alumina. Preferred carrier materials have an apparent bulk density of about 0.3 to about 0.7 g/cc. and surface area characteristics such that the average pore diameter is about 20 to 300 Angstroms, the pore volume is about 0.1 to about 1 cc/g. and the surface area is about 100 to about 500 m$^2$/g. In general, best results are typically obtained with a gamma-alumina carrier material which is used in the form of spherical particles having: a relatively small diameter (i.e., typically about 1/16 inch), an apprent bulk density of about 0.5 to about 0.6 g/cc., a pore volume of about 0.4 ml/g., and a surface area of about 175 m$^2$ /g.

The preferred alumina carrier material may be prepared in any suitable manner and may be synthetically prepared or natural occurring. Whatever type of alumina is employed it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide to a salt of aluminum such as aluminum chloride, aluminum nitrate, etc., in an amount to form an aluminum hydroxide gel which upon drying and calcining is converted to alumina. The alumina carrier may be formed in any desired shape such as sheres, pills, cakes, extrudates, powders, granules, tablets, etc., and utilized in any desired size. For the purpose of the present invention a particularly preferred form of alumina is the sphere; and alumina spheres may be continuously manufactured by the well known oil drop method which comprises: forming an alumina hydrosol by any of the techniques taught in the art and preferably by reacting aluminum metal with hydrochloric acid, combining the resulting hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 150° to about 205°C. and subjected to a calcination procedure at a temperature of about 455°to about 750°C. for a period of about 1 to about 20 hours. This treatment effects conversion of the alumina hydrogel to the corresponding crystalline gamma-alumina. See the teachings of U.S. Pat. No. 2,620,314 for additional details.

One essential constituent of the catalyst of the present invention is a germanium component. It is an essential feature of the catalyst that substantially all of the germanium component is present in the catalyst in an oxidation state above that of the elemental metal. This component may exist within the composite as a compound such as the oxide, sulfide, halide, oxychloride, aluminate, etc., or in combination with the carrier material or other ingredients of the composite. Although it is not intended to restrict the composition of the catalyst by this explanation, it is believed that best results are obtained when the germanium component is present in the composite in the +2 or +4 oxidation state, with the +4 oxidation state being preferred. Preferably, the germanium component is used in an amount sufficient to result in the final catalytic composite containing, on an elemental, Friedel-Crafts metal halide-free basis, about 0.01 to about 5 weight percent germanium with best results typically obtained with about 0.05 to about 2 weight percent germanium.

This germanium component may be incorporated in the catalyst composite in any suitable manner known to the art to result in a uniform dispersion of the metal moiety throughout the carrier material, e.g., by coprecipitation or cogellation with the porous carrier material, ion-exchange with the gelled carrier material, or impregnation of the carrier material either after or before it is dried and calcined. Any conventional method for uniformly distributing a metallic component in a catalytic composite may be employed. The particular method of incorporation used is not deemed to be an essential feature of the preparation of the composite. One method of incorporating the germanium component into the catalytic composite involves coprecipitating the germanium component during the preparation of the preferred carrier material, alumina. This method typically involves the addition of a suitable germanium compound such as germanium tetrachloride or finely divided germanium oxide to the alumina hydrosol and then combining the hydrosol with a suitable gelling agent and dropping the resulting mixture into an oil bath, etc., as explained in detail hereinbefore. After drying and calcining the resulting gelled carrier material there is obtained an intimate combination of alumina and germanium oxide. A preferred method of incorporating the germanium component into the catalytic composite involves utilization of a soluble, decomposable compound of germanium to impregnate the porous carrier material. In general, the solvent used in this impregnation step is selected on the basis of its capacity to dissolve the desired germanium compound and is preferably an aqueous, acidic solution. The germanium component may be added to the carrier material by commingling the latter with an aqueous, acidic solution of suitable germanium salt or suitable compound of germanium such as germanium oxide, germanium tetraethoxide, germanium tetrapropoxide, germanium tetrachloride, germanium difluoride, germanium tetrafluoride, germanium di-iodide, germanium monosulfide and the like compounds. One particularly preferred impregnation solution comprises nascent germanium metal dissolved in chlorine water to yield a germanium oxychloride. A second preferred impregnation solution comprises germanium tetrachloride dissolved in an anhydrous alcohol such as ethanol or propanol. In general, the germanium component can be impregnated either before, at the same time, or after the other metallic components are added to the carrier material; however, excellent results are obtained when the germanium component is impregnated simultaneously with the other metallic components. A preferred impregnation solution comprises chloroplatinic acid, hydrogen chloride, chloroiridic acid and germanium tetrachloride dissolved in ethanol. Best results are believed to be obtained when this component exists in the composite as germanium oxide.

Regardless of which germanium compound is used in the preferred impregnation step, it is important that the germanium component be uniformly distributed throughout the carrier material. In order to achieve this objective it is necessary to maintain the pH of the impregnation solution in a range of about 1 to about 7 and to dilute the impregnation solution to a volume which approximates the volume of the carrier material which is impregnated. It is preferred to use a volume ratio of impregnation solution to carrier material of at least 0.5:1 and preferably about 1:1 to about 10:1 or more. Similarly, it is preferred to use a relatively long contact time during the impregnation step ranging from about one quarter hour up to about one half hour or more before drying to remove excess solvent in order to insure a high dispersion of the germanium component through the carrier material. The mixture of impregnation solution and carrier material is, likewise, preferably constantly agitated during this preferred impregnation step.

A second essential ingredient of the catalyst is the platinum or palladium component. The use of platinum or palladium, or mixtures thereof, as a second component of the present composite are included. It is an essential feature of the catalyst that substantially all of this platinum or palladium component exists within the final catalytic composite in the elemental metallic state. Generally, the amount of this component present in the final catalyst composite is small compared to the quantities of the other components combined therewith. In fact, the platinum or palladium component generally will comprise about 0.01 to about 2 weight percent of the final catalytic composite, calculated on an elemental, Friedel-Crafts metal halide-free basis. Excellent results are obtained when the catalyst contains about 0.05 to about 1 weight percent of platinum or palladium metal.

This platinum or palladium component may be incorporated in the catalytic composite in any suitable manner known to result in a relatively uniform distribution of this component in the carrier material such as coprecipitation or cogellation, ion-exchange, or impregnation. The preferred method involves the utilization of a soluble, decomposable compound of platinum or palladium to impregnate the carrier material in a relatively uniform manner. For example, this component may be added to the support by commingling the latter with an aqueous solution of chloroplatinic or chloropalladic acid. Other water-soluble compounds of platinum or palladium may be employed in impregnation solutions. These include ammonium chloroplatinate, bromoplatinic acid, platinum dichloride, platinum tetrachloride hydrate, platinum dichlorocarbonyl dichloride, dinitrodiaminoplatinum, palladium chloride, palladium nitrate, palladium sulfate, etc. The utilization of a platinum or palladium chloride compound, such as chloroplatinic or chloropalladic acid, is preferred since it facilitates the incorporation of both the platinum or palladium component and at least a minor quantity of the preferred halogen component in a single step. Hydrogen chloride or the like acid is also generally added to the impregnation solution in order to further facilitate the incorporation of the halogen component and the uniform distribution of the metallic component throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

Another essential ingredient of the catalyst composite is an iridium component. It is of fundamental importance that substantially all of the iridium component exist within the catalytic composite of the present invention in the elemental state and the subsequently described reduction procedure is designed to accomplish this objective. The iridium component may be utilized in the composite in any amount which is catalytically effective, with the preferred amount being about 0.01 to about 2 weight percent thereof, calculated on an elemental iridium basis. Typically best results are obtained with about 0.05 to about 1 weight percent iridium. It is additionally preferred to select the specific amount of iridium from within this broad weight range as a function of the amount of the platinum or palladium component, on an atomic basis, as explained hereinafter.

The iridium component may be incorporated into the catalytic composite in any conventional manner which results in a relatively uniform dispersion of iridium in the carrier material. It may be added at any stage of the preparation of the composite, either during preparation of the carrier material or thereafter. The precise method of incorporation used is not critical. Best results are thought to be obtained when the iridium component is relatively uniformly distributed throughout the carrier material, and the preferred procedures are those known to result in a composite having this relatively uniform distribution. One acceptable preocedure for incorporating this component into the composite involves cogelling or coprecipitating the iridium component during the preparation of the preferred carrier material, alumina. This procedure usually comprehends the addition of a soluble, decomposable compound of iridium such as iridium tetrachloride to the alumina hydrosol before it is gelled. The resulting mixture is then finished by conventional gelling, aging,, drying and calcination steps as explained hereinbefore. A preferred way of incorporating this component is an impregnation step wherein the porous carrier material is impregnated with a suitable iridium-containing solution either before, at the same time as, or after the carrier material is calcined. Preferred impregnation solutions are aqueous solutions of water soluble, decomposable iridium compounds such as iridium tribromide, iridium dichloride, iridium tetrachloride, iridium oxalic acid, iridium sulfate, potassium iridochloride, chloroiridic acid and the like compounds. Best results are ordinarily obtained when the impregnation solution is an aqueous solution of chloroiridic acid or sodium chloroiridate. This component can be added to the carrier material, either before, at the same time as, or after the other metallic components are combined therewith. Best results are usually achieved when this component is added simultaneously with the other metallic components. Excellent results are obtained with a one-step impregnation procedure using an aqueous solution comprising chloroplatinic or chloropalladic acid, chloroiridic acid, hydrochloric acid and germanium tetrachloride dissolved in anhydrous alcohol.

It is essential to incorporate a halogen component into the catalytic composite of the present invention. Although the precise form of the chemistry of the association of the halogen component with the carrier material is not entirely known, it is customary in the art to refer to the halogen component as being combined with the carrier material or with the other ingredients of the catalyst in the form of the halide (e.g., as the chloride). This combined halogen may be either fluorine, chlorine, iodine, bromine, or mixtures thereof. Of these, fluorine and, particularly, chlorine are preferred for the purposes of the present invention. The halogen may be added to the carrier material in any suitable manner, either during preparation of the support or before or after the addition of the other components. For example, the halogen may be added to the carrier at any stage of the preparation of the carrier material or after calcination as an aqueous solution of a suitable, decomposable, halogen-containing compound such as hydrogen fluoride, hydrogen chloride, hydrogen bromide, ammonium chloride, etc. The halogen component or a portion thereof, may be combined with the carrier material during the impregnation of the latter with the platinum or palladium or iridium components e.g., by use of a mixture of chloroplatinic acid and hydrogen chloride. In another embodiment, the alumina hydrosol which is typically utilized to form the preferred alumina carrier material may contain halogen and thus contribute at least a portion of the halogen component to the final composite. It is generally preferred to utilize amounts of halogen in the catalyst of less than about 10 weight percent halogen calculated on an elemental basis, and more preferably about 0.1 to about 3.5 weight percent.

Regarding the preferred amounts of the various metallic components of the catalyst, the amounts of the iridium component and the germanium component may be specified as a function of the amount of the platinum or palladium component. On this basis, the amount of the iridium component is ordinarily selected so that the atomic ratio of iridium to platinum or palladium metal contained in the composite is about 0.1:1 to about 2:1, with the preferred range being about 0.25:1 to about 1.5:1. Similarly, the amount of the germanium component is ordinarily selected to produce a composite containing an atomic ratio of germanium to platinum or palladium metal of about 0.3:1 to about 10:1, with the preferred range being about 0.6:1 to about 6:1.

The "total metals content" is defined to be the sum of the platinum or palladium component, the iridium component and the germanium component, calculated on a Friedel-Crafts metal halide-free, elemental metal basis. Good results are ordinarily obtained with the subject catalyst when the total metals content is fixed at a value of about 0.15 to about 3 weight percent, with best results ordinarily achieved at a metals loading of about 0.3 to about 2 weight percent.

Regardless of the details of how the above-described metals components of the catalyst are combined with the porous carrier material, the resulting composite generally will be dried at a temperature of about 95° to about 315°C. for a period of at least about 2 to about 24 hours or more, and calcined or oxidized at a temperature of about 370° to about 595°C. in an air atmosphere for a period of about 0.5 to about 10 hours in order to convert substantially all of the metallic components substantially to the oxide form. Because a halogen component is utilized in the catalyst, best results are generally obtained when the halogen content of the catalyst is adjusted during the calcination step by including a halogen or a halogen containing compound in the air atmosphere utilized. In particular, when the halogen component of the catalyst is chlorine, it is preferred to use a mole ratio of $H_2O$ to $HC_1$ of about 5:1 to about 100:1 during at least a portion of the calcination step in order to adjust the final chlorine content of the calcined composite to a range of about 0.1 to about 3.5 weight percent.

The resulting calcined composite is then impregnated with another essential ingredient of the catalyst of the present invention, the Friedel-Crafts metal halide component. Aluminum chloride is particularly preferred for use as the Friedel-Crafts metal halide component in the present catalyst. Other suitable metal halides include aluminum bromide, ferric chloride, ferric bromide, zinc chloride, beryllium chloride, etc.

The presence of chemically combined hydroxyl groups in the refractory inorganic oxide allows a reaction to occur between the Friedel-Crafts metal halide and the hydroxyl group of the carrier material. For example, aluminum chloride reacts with the hydroxyl groups of the preferred alumina carrier material to yield $Al-O-AlCl_2$ active centers which enhance the catalytic behavior of the composite. It is desired that the combined halogen component be present in the calcined composite within the lower end of the 0.1 to 10 weight percent halogen range. This range of combined halogen content substitutes to some degree for the hydroxyl groups which are necessary for reaction of the carrier material with the Friedel-Crafts metal halide component. This prevents to a small extent, reaction between the Friedel-Crafts metal halide and the carrier material. Some halogen must be present, however, in order to insure that the germanium component remains in its dispersed oxidation state in the catalyst.

The Friedel-Crafts metal halide may be impregnated onto the calcined composite containing combined hydroxyl groups by the sublimation of the Friedel-Crafts metal halide onto the calcined composite under conditions such that the sublimed Friedel-Crafts metal halide is combined with the hydroxyl groups of the calcined composite. This reaction is typically accompanied by the elimination of about 0.5 to about 2.0 moles of hydrogen chloride per mole of Friedel-Crafts metal halide reacted with the carrier material. For example, in the case of subliming aluminum chloride, which sublimes at about 184°C., suitable impregnation temperatures range from about 190° to about 700°C., with a preferable range being between about 200° and about 600°C. The sublimation can be conducted at atmospheric pressure or under increased pressure and in the presence or absence of diluent gases such as hydrogen or light paraffinic hydrocarbons or both. The impregnation of the Friedel-Crafts metal halide may be conducted batch wise, but a preferred method for impregnating the calcined composite is to pass sublimed $AlCl_3$ vapors, in admixture with an inert gas such as hydrogen, through a calcined catalyst bed. This method both continuously deposits and reacts the aluminum chloride and also removes the evolved HCl.

The amount of Friedel-Crafts metal halide combined with the calcined composite may range from about 1 weight percent up to about 100 weight percent of the Friedel-Crafts metal halide-free, calcined composite. The final composite containing the sublimed Friedel-Crafts metal halide is treated to remove the unreacted Friedel-Crafts metal halide by subjecting the composite to a temperature above the sublimation temperature of the Friedel-Crafts metal halide for a time sufficient to remove from the composite any unreacted Friedel-Crafts metal halide. In the case of $AlCl_3$, temperatures of about 400° to about 600°C., and times of from about 1 to about 48 hours are sufficient.

It is an essential feature of the catalyst employed in the process of the present invention that the resultant catalytic composite is subjected to a substantially water-free reduction step prior to its use in the isomerization of hydrocarbons. This step is designed to reduce the platinum or palladium and iridium components to the corresponding metals selectively and to insure a uniform and finely divided dispersion of these metallic components throughout the carrier material, while maintaining the germanium component in a positive oxidation state. Preferably, substantially pure and dry hydrogen (i.e., less than 20 vol. ppm. $H_2O$) is used as the reducing agent in this step. The reducing agent is contacted with the catalyst at conditions including a temperature of about 435° to about 650°C. and a period of time of about 0.5 to 2 hours effective to reduce substantially all of the platinum or palladium and iridium components to their elemental metallic state while maintaining the germanium component in an oxidation state above that of the elemental metal. This reduction treatment may be performed in situ as part of a startup sequence if precautions are taken to predry the isomerization unit to a substantially water-free state and if substantially water-free hydrogen is used.

The resulting reduced catalytic composite may, in some cases, be beneficially subjected to a presulfiding operation designed to incorporate in the catalytic composite from about 0.05 to about 0.5 weight percent sulfur, calculated on an elemental, Friedel-Crafts metal halide-free basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the selectively reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 10° up to about 595°C. or more. It is generally a good practice to perform this presulfiding step under substantially water-free conditions.

According to the present invention, an isomerizable hydrocarbon charge stock, preferably in admixture with hydrogen, is contacted with a catalyst of the type hereinbefore described in a hydrocarbon isomerization zone. Contacting may be effected using the catalyst in a fixed bed system, a moving bed system, a fluidized bed system, or in a batch type operation. In view of the danger of attrition loss of the valuable catalyst and of operational advantages, it is preferred to use a fixed bed system. In this system, a hydrogen-rich gas and the charge stock are preheated by suitable heating means to the desired reaction temperature and then passed into an isomerization zone containing a fixed bed of the catalyst type previously characterized. The conversion zone may be one or more separate reactors with suitable means therebetween to insure that the desired isomerization temperature is maintained at the entrance to each zone. It is to be noted that the reactants may be contacted with the catalyst bed in either upward, downward, or radial flow fashion, and that the reactants may be in the liquid phase, a mixed liquid-vapor phase, or vapor phase when contacted with the catalyst, with best results obtained in a vapor phase.

Isomerization of isomerizable olefinic or saturated hydrocarbons is preferably effected in a continuous downflow fixed bed system. One preferred method is to pass the hydrocarbons continuously, preferably commingled with about 0.1 to about 10 moles or more of hydrogen per mole of hydrocarbon, to an isomerization reaction zone containing the catalyst, and to maintain the zone at proper isomerization conditions such as a temperature in the range of about 0° to about 425°C. or more and a pressure of about atmospheric to about 100 atmospheres or more. The hydrocarbon is passed over the catalyst at a liquid hourly space velocity (defined as volume of liquid hydrocarbon passed per hour per volume of catalyst) of from about 0.1 to about 10 hr.$^{-1}$ or more. In addition, diluents such as argon, nitrogen, etc., may be present. The isomerized product is continuously withdrawn, separated from the reactor effluent, and recovered by conventional means, preferably fractional distillation, while the unreacted starting material may be recycled to form a portion of the feed stock.

Isomerization of an isomerizable alkylaromatic hydrocarbon is preferably effected by contacting the alkylaromatic, in a reaction zone containing the hereinbefore described catalyst as a fixed catalyst bed by passing the hydrocarbon in a down-flow fashion through the bed, while maintaining the zone at proper alkylaromatic isomerization conditions such as a temperature in the range from about 0° to about 600°C. or more, and a pressure of atmospheric to about 100 atmospheres or more. The hydrocarbon is employed, preferably in admixture with hydrogen at a hydrogen to hydrocarbon mole ratio of about 1:1 to about 25:1 or more, and at a liquid hourly hydrocarbon space velocity of about 0.1 to about 20 hr.$^{-1}$ or more. Inert diluents such as nitrogen, argon, etc., may be present. The isomerized product is continuously withdrawn, separated from the reactor effluent by conventional means including fractional distillation or crystallization, and recovered.

The following working examples are given to illustrate further the preparation of the trimetallic catalytic composite utilized in the process of the present invention and the employment of the catalyst in isomerization of hydrocarbons. It is to be understood that the examples are illustrative rather than restrictive.

EXAMPLE I

This example demonstrates a particularly good method of preparing the preferred catalytic composite utilized in the process of the present invention.

An alumina carrier material comprising 1/16 inch spheres is prepared by forming an aluminum hydroxyl chloride sol by dissolving substantially pure aluminum pellets in a hydrochloric acid solution, adding hexamethylenetetramine to the resulting sol, gelling the resulting solution by dropping it into an oil bath to form spherical particles of an aluminum hydrogel, aging and washing the resulting particles and finally drying and calcining the aged and washed particles to form spherical particles of gamma-alumina containing about 0.3 weight percent combined chloride. Additional details as to the method of preparing the preferred carrier material are given in the teachings of U.S. Pat. No. 2,620,314.

A measured amount of germanium tetrachloride is dissolved in anhydrous ethanol. The resulting solution is then aged at room temperature until an equilibrium condition is established therein. An aqueous solution containing chloroplatinic acid, chloroiridic acid and hydrogen chloride is then prepared. The two solutions are then intimately admixed and used to impregnate the gamma-alumina particles in amounts, respectively, calculated to result in a final composite containing, on an elemental basis, 0.375 weight percent platinum, 0.375 weight percent iridium and 0.5 weight percent germanium. In order to insure uniform distribution of the metallic components throughout the carrier material, the amount of hydrogen chloride corresponds to about 2 weight percent of the alumina particles. This impregnation step is performed by adding the carrier material particles to the impregnation mixture with constant agitation. In addition, the volume of the solution is approximately the same as the volume of the carrier material particles. The impregnation mixture is maintained in contact with the carrier material particles for a period of about one-half hour at a temperature of about 21°C. Thereafter, the temperature of the impregnation mixture is raised to about 108°C. and the excess solution is evaporated during a period of about one hour. The resulting dried particles are then subjected to a calcination treatment in an air atmosphere at a temperature of about 496°C. for about 1 hour. The calcined spheres are then contacted with an air stream containing $H_2O$ and HCO in a mole ratio of about 40:1 for about 4 hours at 524°C. in order to adjust the halogen content of the catalyst particles to a value of about 0.90. The resulting particles are analyzed and found to contain, on an elemental basis, about 0.375 weight percent platinum, about 0.375 weight percent iridium, about 0.5 weight percent germanium and about 0.85 weight percent chloride. The atomic ratio of germanium to platinum is found to be 3.56:1, and the atomic ratio of iridium to platinum is found to be 1.02:1. The calcined particles are placed in a glass lined rotating autoclave along with anhydrous aluminum chloride which is added to the autoclave in the amount of 3 parts, by weight, of aluminum chloride for each 4 parts of the calcined catalyst particles added. The autoclave is sealed, pressured with 25 psig. of hydrogen, and heated and rotated for 2 hours at 300°C. The autoclave is then allowed to cool and is decompressed through a caustic scrubber, opened and the final composite removed therefrom. An analysis of the composite removed from the autoclave indicates about a 15 weight percent gain based on the original calcined composite, indicating an amount of aluminum chloride sublimed onto the catalyst of an equivalent weight percent. The caustic scrubber is found to have adsorbed hydrogen fluoride equivalent to about 5.0 weight percent of the calcined composite, which corresponds to about 0.8 moles of HCl evolved per mole of aluminum chloride reacted with the calcined composite.

Thereafter, the resulting catalyst particles are subjected to a dry prereduction treatment designed to reduce the platinum and iridium components to the elemental state, while maintaining the germanium component in a positive oxidation state, by contacting the composite for one hour with a substantially pure hydrogen stream which contains less than 5 volume ppm. $H_2O$ at a temperature of about 565°C. and a pressure slightly above atmospheric. A flow rate of the hydrogen stream through the catalyst particles is used which corresponds to a gas hourly space velocity of about 720 hrs.$^{-1}$.

EXAMPLE II

A portion of the catalyst prepared in Example I is placed, as a catalytic composite, in a continuous flow, fixed bed isomerization plant of conventional design. The charge stock, containing on a weight percent basis, 20.0 percent ethylbenzene, 10.0 percent para-xylene, 50.0 percent meta-xylene, and 20.0 percent ortho-xylene is commingled with about 8 moles of hydrogen per mole of hydrocarbon, heated to 400°C., and continuously charged at 4.0 hr.$^{-1}$ liquid hourly space velocity (LHSV) to the reactor which is maintained at a pressure of about 400 psig. and 400°C. The resulting product evidences essentially equilibrium conversion to para-xylene with only insignificant amounts of cracked products thus indicating an efficient alkylaromatic isomerization catalyst.

EXAMPLE III

A portion of the catalyst produced by the method of Example I is placed in a continuous flow, fixed bed isomerization plant of conventional design as utilized in Example II. Substantially pure meta-xylene is used as a charge stock. The charge stock is commingled with about 8 moles of hydrogen per mole of hydrocarbon, heated to about 390°C., and continuously charged to the reactor which is maintained at a pressure of about 300 psig. Substantial conversion of meta-xylene to para-xylene is obtained ... i.e., greater than 80 percent of equilibrium.

EXAMPLE IV

A catalyst identical to that produced in Example I but containing only 0.40 weight percent combined chloride, on an elemental Friedel-Crafts metal halide-free basis, is used to isomerize 1-butene in an appropriate isomerization reactor, at a reactor pressure of about 500 psig. and a reactor temperature of about 140°C. Substantial conversion to 2-butene is observed.

EXAMPLE V

The same catalyst as utilized in Example IV is charged to an appropriate, continuous isomerization reactor of conventional design maintained at a reactor pressure of about 1000 psig. and a reactor temperature of about 180°C. 3-methyl-1-butene is continuously passed to this reactor with substantial conversion to 2-methyl-2-butene being observed.

EXAMPLE VI

A catalyst, identical to that catalyst produced in Example I except that the gamma-alumina particles are contacted with hydrogen fluoride to provide a 2.9 weight percent combined fluoride content in the catalyst, is placed in an appropriate continuous isomerization reactor of conventional design maintained at a reactor pressure of about 300 psig. and a reactor temperature of about 200°C. Normal hexane is continuously charged to the reactor and an analysis of the product stream shows substantial conversion to 2,2-dimethylbutane, 2,3-dimethylbutane, 2-methylpentane, and 3-methylpentane.

EXAMPLE VII

A portion of the catalyst prepared in Example I is placed in an appropriate continuous isomerization apparatus and used to isomerize normal butane at a reactor pressure of 300 psig., a 0.5 hydrogen to hydrocarbon mole ratio, a 1.0 liquid hourly space velocity, and a reactor temperature of 230°C. Substantial conversion of normal butane to isobutane is observed ... i.e., approximately a conversion of normal butane to isobutane of about 45 weight percent of the original butane charged.

EXAMPLE VIII

A portion of the catalyst prepared in Example I is placed in an appropriate continuous isomerization reactor maintained at a reactor temperature of about 210°C. and a reactor pressure of about 250 psig. Methylcyclopentane is continuously passed to this reactor with a substantial conversion to cyclohexane being observed.

I claim as my invention:

1. A catalytic composite consisting essentially of a refractory inorganic oxide having combined therewith, on a Friedel-Crafts metal halide-free basis, about 0.01 to about 2 weight percent platinum or palladium, about 0.01 to about 2 weight percent iridium, about 0.01 to about 5 weight percent germanium, and about 0.1 to about 3.5 weight percent halogen in halide form, calculated on an elemental basis, and about 1.0 to about 100 weight percent Friedel-Crafts metal halide, wherein the platinum or palladium, iridium and germanium are uniformly dispersed throughout the refractory inorganic oxide, wherein substantially all of the platinum or palladium and iridium are present in the corresponding metallic states and wherein substantially all of the germanium is present in the form of the oxide, sulfide, halide, oxychloride or aluminate.

2. A composite as defined in claim 1 wherein the Friedel-Crafts metal halide is anhydrous aluminum chloride.

3. A composite as defined in claim 2 wherein the refractory inorganic oxide is alumina.

4. A composite as defined in claim 1 wherein the halogen is in chloride form.

5. A composite as defined in claim 1 wherein the atomic ratio of germanium to platinum or palladium contained in the composite is about 0.3:1 to about 10:1.

6. A composite as defined in claim 1 wherein the atomic ratio of iridium to platinum or palladium contained in the composite is about 0.1:1 to about 2:1.

7. A composite as defined in claim 1 wherein the catalytic composite is sulfided to contain about 0.05 to about 0.5 weight percent sulfur, calculated on an elemental, Friedel-Crafts metal halide-free basis.

8. A composite as defined in claim 1 wherein substantially all of the germanium is present in the catalytic composite as germanium oxide.

9. A composite as defined in claim 1 wherein the composite contains, on a Friedel-Crafts metal halide-free, elemental basis, about 0.05 to about 1 weight percent platinum, about 0.05 to about 1 weight percent iridium, about 0.05 to about 2 weight percent germanium and about 0.5 to about 1.5 weight percent halogen.

* * * * *